(12) United States Patent
Johansen

(10) Patent No.: US 9,335,330 B2
(45) Date of Patent: May 10, 2016

(54) METHOD FOR DETERMINING HEALTH STATUS BY ANALYZING ANALYTES

(75) Inventor: Knut Johansen, Linköping (SE)

(73) Assignee: Scientific Engineering QED, Linkoping (SE)

( * ) Notice: Subject to any disclaimer, the term of this patent is extended or adjusted under 35 U.S.C. 154(b) by 920 days.

(21) Appl. No.: 12/456,037

(22) Filed: Jun. 10, 2009

(65) Prior Publication Data

US 2009/0263827 A1 Oct. 22, 2009

Related U.S. Application Data

(63) Continuation of application No. PCT/SE2007/050981, filed on Dec. 12, 2007.

(30) Foreign Application Priority Data

Dec. 12, 2006 (SE) .................................... 0602683

(51) Int. Cl.
| | | |
|---|---|---|
| *G01N 33/48* | (2006.01) | |
| *G01N 31/00* | (2006.01) | |
| *G06G 7/48* | (2006.01) | |
| *G06G 7/58* | (2006.01) | |
| *G01N 33/68* | (2006.01) | |

(52) U.S. Cl.
CPC ...... *G01N 33/6893* (2013.01); *G01N 2800/324* (2013.01)

(58) Field of Classification Search
CPC .. A61B 5/7242; A61B 5/0436; F04B 49/065; A63B 71/0686
See application file for complete search history.

(56) References Cited

U.S. PATENT DOCUMENTS

| | | |
|---|---|---|
| 5,382,515 A | 1/1995 | Shah et al. |
| 6,033,364 A | 3/2000 | Ohman et al. |
| 6,662,114 B1 | 12/2003 | Christenson et al. |

FOREIGN PATENT DOCUMENTS

| | | |
|---|---|---|
| EP | 0 962 878 A2 | 12/1999 |
| EP | 1 102 197 A2 | 5/2001 |
| WO | WO 97/48327 | 12/1997 |
| WO | WO 02/089656 A2 | 11/2002 |
| WO | WO 03/016910 A1 | 2/2003 |
| WO | WO 2004/059293 A2 | 7/2004 |
| WO | WO 2006/120391 A1 | 11/2006 |

OTHER PUBLICATIONS

Yamaoka et al. (Journal of Pharmacokinetics and Biopharmaceutics, 1978, 6(2), 165-175).*
Elkind et al. (Science Daily, Oct. 24, 2006, 1-2).*

(Continued)

*Primary Examiner* — Larry D Riggs, II
(74) *Attorney, Agent, or Firm* — Robert P. Michal, Esq.; Carter, DeLuca, Farrell & Schmidt, LLP

(57) ABSTRACT

A method to extract information from samples taken at different times from a mammalian. These samples are analyzed with respect to one or more analytes giving one or more responses, creating one or more response curves. From this/these response curves is/are changes in the responses calculated as slope, curvatures or mathematical functions. This is especially useful for early detection of acute myocardial infarction.

19 Claims, 9 Drawing Sheets

(56) References Cited

OTHER PUBLICATIONS

Secchiero et al. (Journal of Clinical Laboratory Analysis, 1995, 9, 359-365).*
Buttner et al. (Stroke, 1997, 28, 1961-1965).*
Search Report mailed Apr. 2, 2008 issued by the International Searching Authority in counterpart International Application No. PCT/SE2007/050981 (4 pages).
Written Opinion mailed Apr. 2, 2008 of the International Searching Authority issued in counterpart International Application No. PCT/SE2007/050981 (4 pages).
Larry H. Berstein, et al., "Creatine Kinase B-Subunit Activity In Serum In Cases of Suspected Myocardial Infarction: A Prediction Model Based on the Slope of MB Increase and Percentage CK-MB Activity," *Clinical Chemistry*, vol. 29, Mar. 1983, Washington, D.C. pp. 590-592 (3 pages).
P.O. Collinson, et al., "Early diagnosis of myocardial infarction by timed sequential enzyme measurements," *Annals of Clinical Biochemistry*, vol. 25, 1988, London, United Kingdom, pp. 376-382 (7 pages).
P.O. Collinson, et al., "Diagnosis of acute myocardial infarction from sequential enzyme measurements obtained within 12 hours of amission to hospital," *Journal of Clinical Pathology*, vol. 42, Nov. 1989, London, United Kingdom, pp. 1126-1131 (6 pages).
S. G. Vijan, et al., "Failure of creatine kinase slope values to reliably predict acute myocardial infarction," *Annals of Clinical Biochemistry*, vol. 28, 1991, London, United Kingdom, pp. 103-104 (2 pages).
P.O. Collinson, et al., "Early diagnosis of acute myocardial infarction by CK-MB mass measurements," *Annals of Clinical Biochemistry*, vol. 29, 1992, London, United Kingdom, pp. 43-47 (5 pages).
Robin T. Vollmer, M.D., et al., "Temporal Creatine Kinase Curves in Acute Myocardial Infarction—Implications of a Good Empiric Fit with the Log-Normal Function," *Clinical Chemistry—American Journal of Clinical Pathology*, vol. 100, No. 3, Sep. 1993, Chicago, Illinois, pp. 293-298 (6 pages).
P. Chattington, et al., "Timed Sequential analysis of creatine kinase in the diagnosis of mycardial infarction in patients over 65 years of age," *Clinical Chemistry—Journal of Clinical Pathology*, vol. 47, Nov. 1994, London, United Kingdom, pp. 995-998 (4 pages).
G. Rutty, et al., "Application of the regression coefficient to timed serial serum creatine kinase measurements in the early diagnosis of myocardial infarction," *Annals of Clinical Biochemistry*, vol. 26, 1989, London, United Kingdom, pp. 558-559 (2 pages)
J. D. Johnston, et al., "MIDAS: Myocardial infarct diagnosis by assessment of slope," *Annals of Clinical Biochemistry*, vol. 30, 1993, London, United Kingdom, pp. 407-409 (3 pages).
Communication dated Dec. 21, 2009 by the European Patent Office in related European Patent Application No. 07852252.1 (6 pages).
Communication Pursuant to Article 94(3) EPC issued Jul. 5, 2012 in related European Patent Application No. 07 852 252.1 (5 pages).
Office Action issued May 21, 2014 by European Patent Office in corresponding EP Patent Appln. No. 07 852 252.1, 6 pages.

* cited by examiner

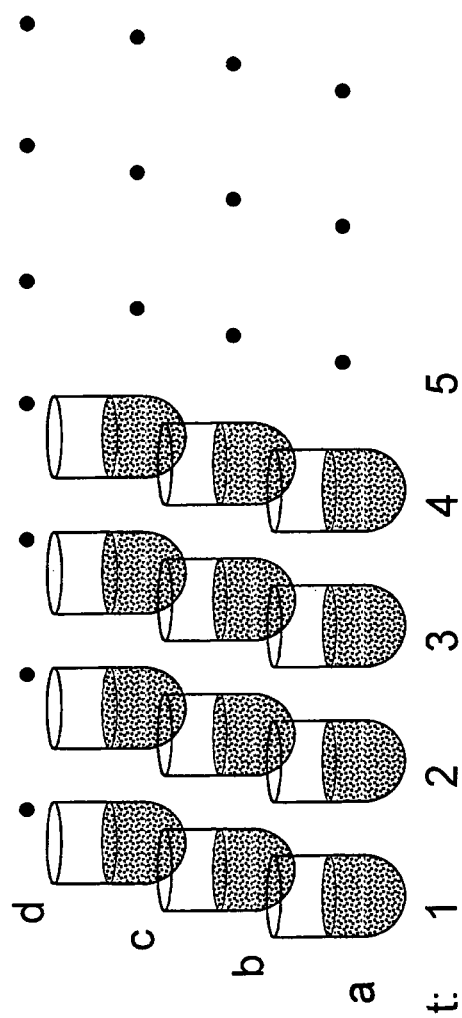
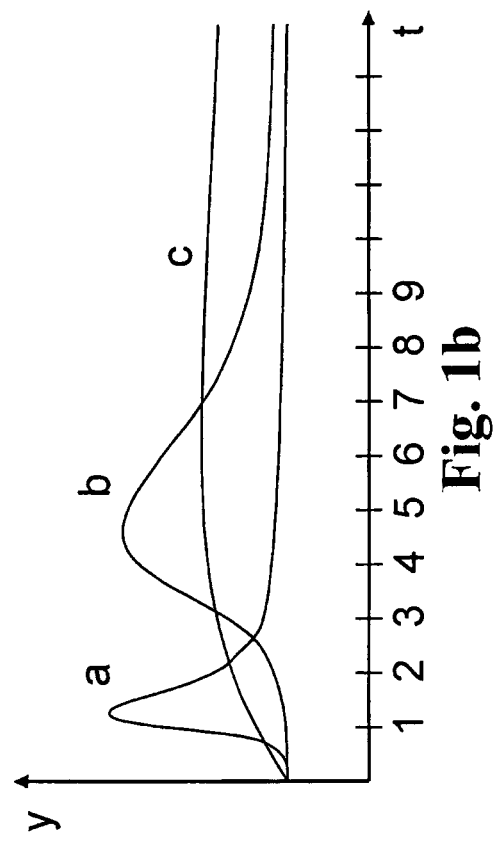
Fig. 1a
Fig. 1b

METHOD FOR DETERMINING HEALTH STATUS BY ANALYZING ANALYTES

CROSS-REFERENCE TO RELATED APPLICATIONS

This is a continuation of International Application PCT/SE2007/050981 filed Dec. 12, 2007, which claims priority under 35 USC 119 of Sweden Patent Application No. SE 062683-5 filed December 12, the entire disclosure of each of which is incorporated herein by reference.

FIELD OF THE INVENTION

The present invention relates to the field of medical diagnosis in general, and in particular it relates to early diagnosis in acute medical conditions.

BACKGROUND INFORMATION

In human beings and animals, many molecules are present in the blood and other body fluids, such as urine and saliva, and these molecules can be used as markers for different diseases or for assessing the general health status. The concentration of these molecules may vary over time in the body, from long time to short time. It is common that the concentration in such body fluids of a specific molecule changes with time due to a disease. A disease may involve a concentration change of several molecules, each with their specific time pattern. Acute myocardial infarction (AMI) is an example where several analytes (molecules) are released on different time scales, and showing different degree of specificity.

Almost all clinical decisions are made upon absolute responses, which have shown to have many limitations. In particular there is a problem in using absolute values in that they must be related to a base line, e.g. values for a healthy person. Since base lines may vary between individuals, absolute values can result in erroneous interpretations of measurements.

Coronary diseases, especially AMI, are the largest factor for human death, and there is a great demand for clinical solutions to improve the treatment for these diseases.

ECG

A very common method for determining AMI in the early phase (within 2 hours from pain onset), is to record an electrocardiogram (ECG). This is a method invented by Willem Einthoven and has been used since the early 1920's. The method involves measuring the electrical potential close to the heart at different points as a function of time for six points, denoted V1 to V6 around the chest, close to the heart. The potential changes versus time emanates from depolarization waves within the heart, emanating from the sinus point. There are three typical pulses, denoted P from auricular contraction, QRS from ventricle contraction, and T from repolarization. At AMI and other cardiac diseases where there is an ischemic (lack of blood circulation) condition there are changes in ECG pattern. However, the changes are very difficult to interpret. Even for a highly trained specialist it is in many cases impossible to determine an AMI. Typical ECG signs for an early AMI are primarily increasing level of the ST segment for the V1 to V5 connections, secondarily a decrease of amplitude and broadening of the Q-wave from V1 to V3 connections, and sometimes a negative T-wave from V2 to V6 connections. In the early phase of AMI, ECG changes are small and difficult to interpret [Jern, 1990].

Other cardiac diseases may show different patterns, e.g. heart failure may show a lower ST-segment. A lower ST-segment may be a sign of lack of oxygen in the heart.

Cardiac Markers

Clinical diagnosis of coronary syndromes have lately been characterized by cardiac markers, patent WO2004059293, and WO03016910. One of the first reliably markers for AMI was CKMB, which has lately been substituted for Troponin I and T. There are many other molecules that are more or less specific as cardiac markers, such as Myoglobin and Lactate Hydro Genase (LHD). Myoglobin is an early marker in that way that it will have peak valued in the blood after typical eight hours after pain onset (time for occlusion). However, myoglobin is present in skeleton muscle and hence not specific to cardiac damage, leading to low specificity for AMI. CKMB is more specific to cardiac damage, but is slower and will lead to a typical peak value after typical 24 hours. Troponin I and C are more specific, but show similar time to peak value. The traditional way to diagnose AMI has been to check the level of the cardiac markers at different times, typical at admission, and after 6 and 12 hours. Unfortunately the diagnosis has been set when the time window for treatment is gone. Since a long time people have measured differences in cardiac enzymes, and Bernsten et al. have taken the slope of CK-MB Clin Chem 1983 29(3) p 590-592. Collingson et al. have showed how slope measurements can be performed as a retrospective diagnosis: Clin. Chem. 1983, 29(3) p 590-592, Ann Clin Biochem, 1988 25 p 376-382, J Clin Pathol 1989, 42 p 1126-31, Ann Clin Biochem 1992, 29 p 34-47, Ann Clin Biochem 1993, 30 p 407-409. Others have done the same, not being able to perform an diagnosis for treatment: Ann Clin Biochem 1989, 26, p 558-559, Ann Clin Biochem 1991, 28 p 103-104, J Clin Pathol 1994, 47 p 995-998. These methods seems to vanish, for many reasons, e.g. the sampling time have been too long due to cost and lack of suitable equipment. The sparse values means that changes in the slopes (i.e. curvatures) will be lost. Logarithmic values have been used in slope calculations, which means that slope values are dependent on time sampling. Moreover, it lead to difficulties to set cut off values.

The markers mentioned have been used to predict the size of necrosis, where total amount released (area under curve) or maximum concentration are used. There are studies where the concentration of CK-MB in blood after an AMI is fitted to a mathematical curve R. Vollmer et al. Am J Clin Pathol, 1993 100, p 293-298. A formula used (Christenson et al) is $y=a*\exp[(-0.5*(\ln t-b)/c)^2]$ (correct formula is probably $y=a*\exp[-0.5*(\ln(t/b)/c)^2]$), where a, b, c are parameters, and t the time. The parameter a is the amplitude, b should be the time to peak maximum, and c is a parameter defining the width. Such functions have been used to evaluate therapies, especially thrombolytic therapy, and predicting clinical outcome related to coronary conditions, in some cases by using the slope of the curve on the descending portion, Christenson et al. U.S. Pat. No. 6,662,114. The formula above has a limitation by letting the ascending and descending portions of the curve be 100% dependent of each other.

Evaluation of more than one cardiac marker has been evaluated using artificial neural networks, patent WO97/48327.

A common problem in previous techniques is the requirement of blood plasma or serum. This means that the sample are treated, which may lead to different behavior, and definitely means that the original concentration of analytes are changed. Moreover, there is likely that there will be a variation in analyte concentration due to the difficulties to perform the treatments exactly the same from tome to time.

Previous methods of measuring cardiac markers have been retrospective, in that manner that response levels and slope levels have been used to see what happened (when the damage is permanent). It is not used prospective. With prospective method, we define it as a method where signals for diagnosis is continuously presented as long as measurements are performed, and proper diagnosis and decision of treatment can continuously be made as health status evolve.

MRI and CT

There are other techniques to detect myocardial infarction, such as magnetic resonance imaging (MRI) and computer tomography (CT). These techniques require large and expensive apparatus and special trained operators, which make them unsuitable to use as a common diagnostic method.

SUMMARY OF THE INVENTION

Because of the poor certainty of e.g. ECG results, there has been a need in the art for better methods yielding quicker results, thereby enabling making diagnosis at an earlier stage than what is currently possible.

The object of the present invention is thus to provide a novel method for providing reliable indications of health status of patient in early stages of a suspected acute medical condition, such as acute myocardial infarction (AMI), stroke, sepsis, surgery etc.

The proposed invention consists of rapid serial measurements of liquid samples from a mammalian with precise time marks, and if necessary, filtration of input signals, and extracting information of the curve shape, such as response levels and/or slope and/or curvature to assist in prospective and/or retroprospective determination of the health status, using one or more response sources, such as different marker molecules.

The method of the present invention generates information in two stages, first: raw data from one or more response sources, e.g. cardiac markers analysed from blood samples, where these responses are mathematically treated to extract information which gives more adequate signals than the response levels themselves. Examples of these signals are slope values and curvature values. A second feature is to use these signals and lump them together, e.g. responses, slopes, and curvatures from one or more analytes to form one or more significant health signals, which are usable as a help for the physician to provide appropriate treatment.

Because the invention gives information about the health status, the proposed method can be used in classification of diseases as well as guidelines during therapeutic treatment.

This object is achieved by the method as defined in claim 1. In particular, by using the invention which involves detecting the trend in the concentration of one or more analytes, in e.g. blood, urine or other body fluids, an early diagnosis is possible. The diagnosis can in this case be performed by trend analysis it self, and also by prediction of later responses, using the recorded data. By using a plurality of analytes the prediction can be further enhanced. In this case different multivariable techniques can be used such as artificial neural networks (ANN) or principal component analysis (PCA) to mention a few.

An advantage of the trend measurements according to the invention is the possibility to cancel different baselines, which may vary between individuals, or at different times for an individual. Thereby a reduction of both false negative (a sick person is declared healthy) and false positive (a healthy person is declared sick) results are achieved. This means that both the clinical sensitivity and specificity are enhanced.

The use of filtering (smoothing of data) will enhance precision of responses and lead to more reliable trends analyzes.

Further scope of applicability of the present invention will become apparent from the detailed description given hereinafter and the accompanying drawings which are given by way of illustration only, and thus not to be considered limiting on the present invention, and wherein

BRIEF DESCRIPTION OF THE DRAWINGS

FIG. 1a. shows schematically how a plurality of analytes, a, b, c, d, etc are monitored at different times, t.

FIG. 1b shows how the concentration, y, of the different analytes a, b, c, etc will form different curves with respect to time, t.

DETAILED DESCRIPTION OF PREFERRED EMBODIMENTS

Figure 2:
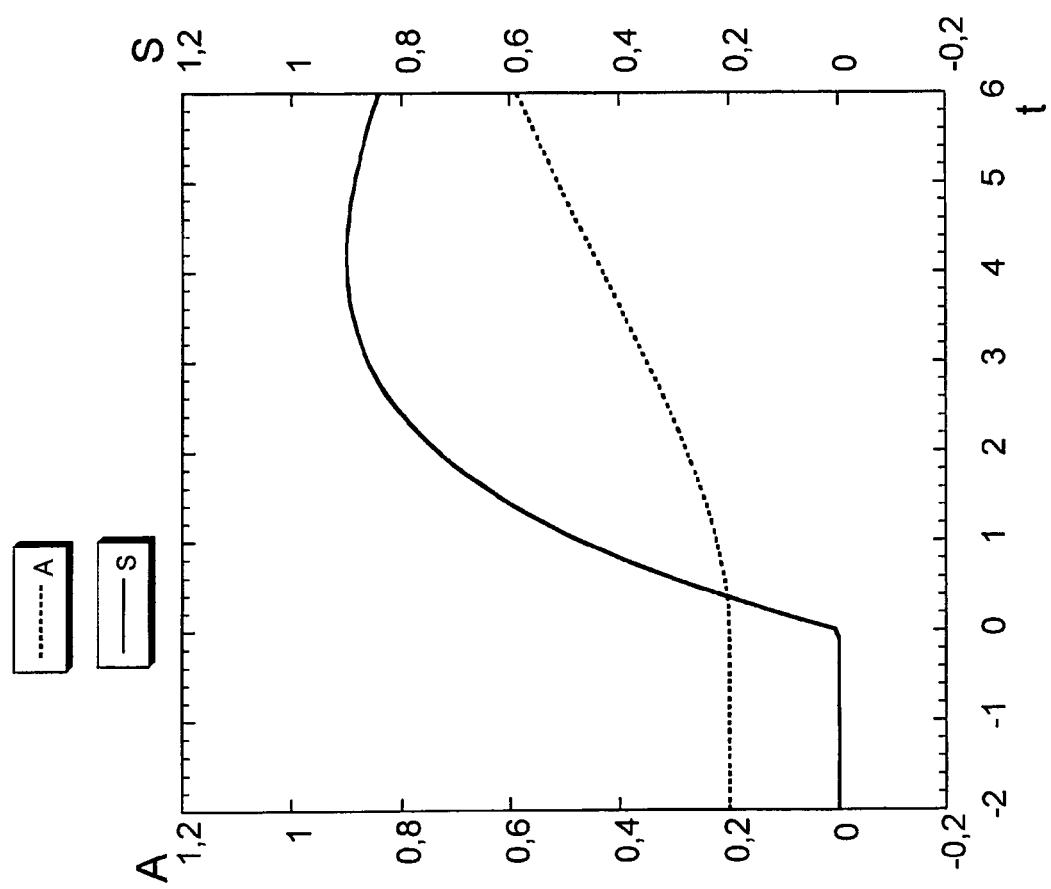
FIG. 2. illustrates a typical behavior for a concentration of the analyte Troponin-I during AMI.

The method according to the present invention takes advantage of changes in the response signal from one or more samples of body fluids, taken at different times, from patients suspected of suffering from a medical condition. Each response signal has then a time mark associated with it. Each response signal will then have two values associated with it, the response level and the time mark or time coordinate. The time mark can emanate from an individual time setting or from a common time base. Using equidistant sampling methods data space can be reduced. The response that is utilized can be from a single analyte or from a plurality of analytes. The basic concept of the invention is to determine changes in response signal by calculating derivatives of first or/and higher orders, and/or to perform curve fitting, whereby slopes, curvatures and coefficients can be determined. The responses can emanate from separate samples or a continuous stream of body fluids.

By calculating the slope the influence of any baseline (i.e. offset) will be cancelled and a more sensitive and specific signal will be obtained for medical conditions changing with time.

There is a demand for early diagnosis of AMI as described in previous sections. A key parameter is the size of the infarction. There is a common opinion that the maximum Troponin concentration is proportional to the infarction size. Unfortunately, when that value is determined, it is too late for treatment. One may think that the whole release of marker (area under curve) is a better prediction, but it has been shown that it is not as accurate as required, still there is a good correlation. Because the curve shape of a marker is similar between patients, a maximum slope at ascending part will have a high correlation to the maximum value, i.e. the maximum slope will be a good estimation of infarction size. Because maximum slope will occur early, it is well suited for decision of therapy. Even earlier will the curve rise from the base line leading to an initial curvature, e.g. second order time derivative of concentration. This maximum curvature value will be highly correlated to the maximum slope and to the maximum concentration, which means that it can be used as a very early signal for AMI. The curvature can also be used to point out where the slope is stable, e.g. at maximum slope value, where the curvature is low or zero.

The invention presents data to perform an early diagnosis. Not only can the data be used for determination of the present health status, but can also be used prospective, i.e. predict the future health status and outcome of medication. Moreover the data presented by the invention can be used retrospective, i.e. determine the history of the health status.

By using more than one analyte a better diagnosis can be performed using e.g. PCA and/or ANNs.

Evaluation

"False negative" means a sick person is declared healthy.
"False positive" means a healthy person is declared sick.
"Specificity"=true negative/(true negative+false positive), i.e. the specificity is a relative number that gives information indicating how well the method/instrument manages to correctly declare a patient healthy among all healthy patients.
"Sensitivity"=true positive/(true positive+false negative), i.e. the sensitivity is a relative number that will tell you how well the method method/instrument manage to correctly declare a patient sick among all sick patients.
"Decision level" means a level of analyte concentration or activity (or the time derivative of analyte concentration, or some other parameter) which is chosen as a threshold to make a decision however a patient is healthy or sick, or what kind of treatment is needed, to mention a few examples.

It can easily be seen that by reducing the decision level the sensitivity will increase, and specificity will decrease, i.e. healthy people will be treated, which can be associated with considerable and severe risks for the patient. In the same way an increase in the decision level the sensitivity will decrease and the specificity will increase, i.e. sick people will not be treated, which of course also may be very dangerous. The decision level has therefore to be chosen with care, often chosen as two times the reference value for healthy persons.

Not only is the medical issues dependent on the specificity and sensitivity, but they will also affect economical issues.

The sensitivity and specificity numbers are not only dependent on the decision level but also on the quality of performed measurements (i.e. accuracy and precision), and also of the method chosen. Precision is defined as the scattering in result from a measurand (sample) with a fixed value, i.e. precision gives no information about how true the reading is. Accuracy is defined as how close a measurement is to the true value. Often, it is much more difficult to obtain high accuracy than a high precision.

If one considers trends, i.e. derivatives, baselines will cancel and accuracy numbers become less important, which means that the method proposed, require less accuracy, which means that simpler and cheaper instruments and handling can be used.

A number that could be of interest to describe is the diagnostic accuracy of a method taking both sensitivity and specificity to account, which can be defined as:

Diagnostic accuracy=(true negative+true positive)/all patients i.e. efficiency shows how effectively the decision level is set and/or the precision/accuracy of the method and equipment. Diagnostic accuracy should not be intermixed with accuracy of the method or apparatus.

However, the most important feature using trend analysis is higher significance for health conditions that are rapidly changing, e.g. AMI, stroke, infections, sepsis, hemostasis during surgery etc.

Trend analysis requires that the precision of readings are acceptable. For trend analysis, the over all precision is not only dependent on the precision in sample concentration or activity, but also in (relative) time determination. Automatic sampling time determination is therefore wanted. The time between samples do not necessary have to be equidistant.

The method preferably uses many samples, for several reasons: the possibility to detect rapid changes in the responses, give fast signals to the clinic, and make the possibilities to do effective filtration to achieve better precision. The proposed sample timing is preferably made by more or less automatic sampling. To reduce variation in slope, curvature and/or function parameters from curve fitting it is necessary to use correct sampling times. The time mark should be as correct as possible, which practically would be in the region of 1 second. However this does not mean that the sample should be taken in 1 second, but the sampling pattern between consecutive samples should be within 1 second. If samples are taken every 10 minutes a 1 second variation leads to a relative error of 1/600, less than 0.2%. A 10 second variation would lead to 1.7% variation, which will influence signal quality. For rapid or acute syndromes e.g. during surgery, 1 minute sampling may be wanted. For AMI probably 10 minute sampling will be satisfactory and diagnosis could be made within 2 hours, which is in the window for treatment. 10 minutes sampling during 2 hours lead to 12 response values for each analyte, which is enough to perform effective filtering and curve analysis. When used as a retrospective diagnosis in AMI it is common to register the peak value for Troponins, which usually occurs in 24 to 48 hours, a sparse sampling is required, e.g. a couple of hours. In a preferred embodiment, although not limited thereto, the rate of change is based on precise sampling times, preferably, but not limited to, less than 1 minute, more preferably less than 10 seconds, most preferably less than 1 second variation of actual sampling time and sampling time used in calculations, and short time intervals between samples, most preferably, but not limited to, between 10 minutes and 30 minutes, and preferably less than one hour in the initial phase.

Automatic sample analysis means that many samples can be analyzed with short time intervals. Sample responses are preferably, but not necessarily, filtered to obtain reduced unwanted variations in response signals. Time constants of filters are chosen not to distort the original long term shape of the response signal. Suitable filtering is averaging, weighted averaging, median filter, finite impulse filter (FIR-filter), and infinite impulse response filter (IIR-filter) to mention a few. The filters can be used in combination with each others, e.g. a median filter is very effective to reduce outlayers, and can be used with the other filters. The use of many sample points at short time intervals will improve signal quality. As a rule of thumb the precision will be better as the square root of the number of samples used in the filtration. Filtration is preferably performed in a moving average fashion, which means that no time information is lost.

Use of untreated samples such as whole blood will eliminate sample variation that is present in formation of blood plasma or serum. Moreover, a preferable embodiment of the invention uses blood directly, which eliminates the need for anticoagulants such as citrate buffer, which will also introduce a variation of the analyte content in the sample.

One embodiment of the invention is when one analyte (molecule) is analyzed at different times. Output from these analyses are analyte concentration at different times, $A(t_n)=A_n$, where A is analyte concentration and $t_n$ is discrete times corresponding to when each sample is taken, and n is an index number. The change in A is defined by a derivative, S:

$$S(t) = \frac{d}{dt}A(t) \qquad (1)$$

Which for the discrete case can be approximated with e.g.:

$$S_n = \frac{A_{n+1} - A_n}{t_{n+1} - t_n} \qquad (2)$$

Another way to calculate the derivative is to fit $A_n$ to a function, and then use the fitted parameters to calculate the derivative. In this case both the function and the derivative will be defined between data points, and not only at discrete points. The function used could be a polynomial e.g. of second order:

$$A(t) = a + b \cdot (t-t_0) + c \cdot (t-t_0)^2$$

The derivative is then:

$$S(t) = b + 2c(t-t_0)$$

The function chosen can consist of exponential functions e.g.:

$$A(t) = a + b\left[\left(1 - e^{\frac{-t}{T_0}}\right)\left(1 - e^{\frac{-t}{T_1}}\right)e^{\frac{-t}{T_2}}\right] \qquad (3)$$

It is important that the function chosen resembles the physical behavior of the sample responses.

Different functions can be used for different analyte samples. Moreover, an automatic procedure can be used to choose among different functions. This means that an ensemble of different functions can be used for different patients and situations, where the best function is chosen automatically by software. Selection can e.g. be based on statistical theory like the F-test, or upon information theory like the Akaide's Information Criteria (AIC) or a corrected AIC (AICc). F-test can be performed on nested functions, i.e. where a function is a subset of the other. AIC can be used on arbitrary functions, and is a preferred embodiment.

It is also possible to use higher order derivatives, i.e. the calculation of response source change is performed by forming higher order derivatives.

Instead of using discrete points for the calculation of derivatives, curve fitting can be used, i.e. measurement data, i.e. the responses, are fitted to one or a plurality of mathematical model/models. In order to further improve the method iterative curve fitting can be performed. In particular the so called Levenberg-Marquardt method is used for iteration. Another alternative method is a simplex method.

Several different mathematical functions can be used for curve fitting, the choice being i.a. dependent on the medical condition and the behavior of the markers. Suitable models, although the invention is not restricted thereto, are a polynomial, a linear equation, a polynomial is of second order, a polynomial is of third order, one or more exponential functions. Suitably, the model consists of at least two exponential functions, or even more. A preferred mathematical model consists of at least three exponential functions. Suitably, at least one of said exponential function will increase with time. In other embodiments at least one of said exponential function will decrease with time. Still further embodiments comprise at least two of said exponential functions which increase with time. Also, it is possible to have at least one of said exponential function increase with time and at least one of said exponential function decrease with time.

In a still further embodiment, the mathematical model includes at least a function of the type $K*(1-\exp(-t/T1))\exp(-t/T2)$, wherein K is a constant and T1 and T2 are characteristic time constants obtained as parameters from curve fitting procedures.

Another possible function is of the form $K*(1-\exp(-t/T0))(1-\exp(-t/T1))\exp(-t/T2)$, wherein K is a constant and T1, T2, T3 are characteristic time constants.

Preferably a decision level is based on the level of one or a plurality of the calculated derivative/derivatives from said responses. In the case of a plurality of decision levels, these are based on the levels of one or a plurality of the response/responses and/or the calculated derivative/derivatives from said responses. Suitably the decision level is based on the level of said calculated second order derivative/derivatives from said responses. Alternatively, said decision levels are based on said response and/or of said calculated slope and/or curvature or functions, e.g. first and/or second order derivative/derivatives from said responses.

For the case where more than one analyte is examined, two or more of the analyte response sources are used to determine a plurality of slopes or derivatives and/or curvature of said functions, e.g. second order derivatives.

Looking at one analyte, two or more of said sensor responses, separated in time, can be used to predict the mathematical function for a value space before, between and/or after said response points. Suitably, the prediction in question is a determination of parameters for a polynomial. The prediction can also be a determination of parameters for one or a plurality of exponential functions. In one embodiment the prediction is a mix of polynomials and exponential functions.

The response in question is suitably analyte concentration or is activity. Many analytes are enzymes, such as creatin kinase, and enzyme activity can be a better marker than the analyte concentration itself.

Medical Status

In order to determine the severity of the health status of a mammal, the responses, slopes and curvatures from one or more analytes are lumped together in a weighted sum fashion, giving at least one output signal. This output signal can be analyzed with two or more threshold levels to obtain different status, e.g. weak disease or severe disease.

The weighted output signal does not limit the use of individual response, slope, and curvature values from individual analytes.

An example: Below a certain threshold value a patient can safely be regarded as healthy. Between this threshold level and another threshold level further examination or precaution is needed. Over the second threshold prompt treatment is needed.

In order to determine one or a plurality of threshold values, the sensor responses and/or derivative values from two or more samples of are used together, e.g. forming a weighted sum.

It can be convenient to use Boolean outputs, and for that purpose derivative values are compared with respective threshold values and Boolean outputs are formed (derivative value under or over threshold). The Boolean output from such comparison of derivative values can suitably be combined into a Boolean network. Such a Boolean network can consist of Boolean functions as OR, AND, XOR (exclusive or), NOR and NAND operators which determine one or a plurality of outputs, which can represent positive, negative, weak positive, weak negative health status.

Preferably the response values and/or derivative values are mathematically combined to produce a multi level output signal, which can be a weighted sum of the response values and/or derivative values. These threshold values or weighting can be dependent on time, and the time dependence is correlated to other clinical indications, e.g. pain onset. For AMI, typically the curvature is weighted high in the beginning, then the slope is weighted high, and finally the absolute response is weighted high.

In one embodiment of the method according to the invention the output value is based on principal component analysis (PCA).

In another embodiment the output value is based on an artificial neural network (ANN).

In the method according to the invention a plurality of functions can be used and at least one is selected for each said sample analyte. Suitably the selection is performed with a F-test. Furthermore, the selection can be performed with Akaike's Information Criteria (AIC) or with the Corrected Akaike's Information Criteria (AICc).

One of many advantages using the slope instead of the response itself is that the size of the damage will be known directly, whereas the size of the damage for absolute responses are given at maximum level, too late for proper treatment.

Apparatus

The apparatus according to the invention, is suitable for determining health status of a mammal by calculation of responses, derivatives of arrays of data points consisting of at least three elements, emanating from response sources from body fluids of the mammal. The apparatus comprises means for measuring response from at least one response source, present in samples of body fluids, repetitively taken from said mammal, wherein a plurality, at least three, of said responses from the same response source are measured at different times; means for precisely determining time marks of said data points; a processing unit, preferably incorporating an embedded arithmetic logic unit (ALU), or a processor, optionally incorporating a floating point unit, for calculating the rate of change over time and/or the rate of change of said rate of change over time of the responses from said response source/response sources, using said precisely determined time marks and said responses.

In an embodiment the apparatus further comprises means for displaying the result/results from said calculation for a prospective and/or retrospective determination of health status.

Thus the apparatus can perform the calculations and signal conditioning and can be a computer, or a dedicated instrument, preferably incorporating an embedded arithmetic logic unit (ALU), or a processor, which preferably, but not necessarily incorporates a floating point unit. Moreover, the same apparatus that quantify the response levels is preferably setting time marks associated to the response levels. The time marks are set with high precision to obtain precise and accurate derivatives. Furthermore the same apparatus quantifying the data from the responses sources is preferably, but not necessarily, the same unit that performs the described signal conditioning and calculation. Embodiments of the apparatus described may incorporate more than one processor or ALU, which may perform different tasks.

The invention will now be further illustrated by way of non-limiting examples of different medical conditions for which the invention is applicable.

EXAMPLES

Example 1

AMI

One of the most common and serious human diseases is the heart-circulatory diseases, like heart failure (coronary insufficiency), unstable angina pectoris (UAP) and acute myocardial infarction (AMI). Whereas the two former diseases are usually treated with a long time medication, AMI is an acute syndrome and has to be treated immediately to avoid permanent heart damage (necrosis). Therefore there is a need to discriminate between the different heart diseases, as well as other causes for chest pain.

There are several indications of AMI: the patient often feels a pain and pressure over the chest for at least 15 minutes, and often pain radiating into the left arm. A feeling of unpleasantness and illness is often common. There seems to be different patterns between male and female patients, where the female patients seem to experience less pain.

However, the symptoms mentioned cannot alone for the basis for a diagnosis of AMI. There are many other situations that cause have similar symptoms, such as muscle damage (rib breakage and Tietze's syndrome, gastrological diseases (oesophagitis, gallstone disease), lung diseases (pneumonia, pleurisy), and psychosomatic pain states, besides heart failure (coronary insufficiency) and UAP.

In accordance with the invention, a patient suspected of suffering from AMI, is subjected to sampling of blood, and the sample is immediately analyzed with respect to a selected number of relevant markers. Measurements are taken sequentially at different times, and on the basis of the trend analysis according to the invention, i.e. calculation of derivatives, the health status of the patient can be evaluated at a very early stage after e.g. a heart attack has taken place.

There are a number of suitable biochemical markers for AMI. The first specific marker used was an isoenzyme, CK-MB (Creatin Kinase—Muscle Brain). Nowadays, the protein Troponin-I is often used due to its specificity to AMI. However, both CK-MB and Troponin-I are slowly leaking into the blood system, with a maximum concentration approximately 24 hours after pain onset. Unfortunately, permanent damage to the heart occurs six hours after pain onset, which means that currently used methods of measuring these analytes are not optimal for deciding a proper treatment.

A early released marker such as Myoglobin (despite it is not very specific) can be analyzed simultaneously with a specific marker such as Troponin to increase sensitivity and specificity.

The proposed method e.g. using slope and/or curvature evaluation, is also very useful to check for the outcome of thrombolytical therapy. If blood clot is solved and reperfusion is reestablished, a rapid change in analyte concentration is expected, leading to fast response in the slope and curvature signal. Based on these results, a better decision information is obtained for further treatment.

In case of AMI it is of uttermost important to open the blocking of the closed coronary vessel to avoid permanent damage (necrosis). It seems that the best method of treating AMI is to perform a PCI (Perkutan Coronary Intervention), which means that the vessel is expanded with a balloon. The balloon is often inserted into the coronary vessels in the heart by passing a guide wire or catheter through the blood vasculature from e.g. the femoral artery in the leg.

Thrombolytica

If there is problem to reach the blocked vessel or it is of other reasons not possible to perform PCI, thrombolytic treatment is necessary, e.g. by streptokinase, tpA (tissue plasminogen activator), APSAC, urokinase, r-PA, TNK-T-PA Staphylokinase. The most popular substances are Streptokinase and t-PA. Streptokinase binds to plasminogen and speeds up the conversion from plasminogen to the enzyme plasmin. Plasmin breaks up fibrin and the clot dissolves. tpA is an enzyme that with fibrin converts plasminogen to plasmin, which dissolves the clot. tpA is a natural substance in the body, produced in the endothelial cells and macro phages. The activation can be inhibited by PAI (plasminogen activation inhibitor).

A non-exhaustive enumeration of suitable markers is the following:

Different markers are used for different situations: initial diagnostics, possible contra indications such as inhibition of thrombolysis, out come of therapy, secondary injuries due to treatment Cardiac Markers Troponin-I (TnI), Troponin-T (TnT), Troponin-C (TnC), isoenzyme Creatine Kinase-Muscle Brain (CK-MB), Myoglobin, Lactate Hydro Genase (LHD) isoenzyme, Myosin light chain (MLC), N-terminal pro-B-type natriuretic peptide (NT-proBNP), pro-B-type natriuretic peptide (proBNP), Fatty Acid Binding Protein (FABP), Glycogen Phosphorylase isoenzyme BB (GPBB), high sensitivity C-reactive protein (CRP), urinary Albumin, Interleukin-6 (IL-6), Ischaemica Modified Albumin (IMA), Aspartat Transaminase (AST), Hydroxybutyrate dehydrogenase (HBD), drop in iron concentration, enzymatic urinary creatine.

Markers that Test for Possible Inhibition of Treatment antibody for streptokinase, Plasminogen, Activation Inhibitor (PAI-1) and, (PAI-2), Makers that Test for Clot Solving Possibility tissue Plasminogen Activator (tPA), urine Plasmin, Activator (uPA), vitronectin or S-protein, C-protein, antithrombin III, Markers for Detection of Stroke: Ischemic or Hemorrhagic Determination S-100 protein.

DETAILED DESCRIPTION OF THE FIGURES

In FIG. 1a shows how a plurality of analytes, a, b, c, d, etc are monitored at different times, t. The analytes a, b, c, etc do not have to be placed in separate vials, but are usually taken in one sample (here separated for clarity). When samples are analyzed, the concentration, y, of the different analytes a, b, c, etc will form different curves with respect to time, t, as shown in FIG. 1b.

FIG. 2 shows one specific marker, Troponin-I, during a condition of AMI. A is the concentration (arbitrary units), S is the slope of A (arbitrary units), and t is the time in hours. Occlusion of blood coronary vessel occurs at time t=0. AMI should be treated as soon as possible, because, after six hours there are permanent cell damage. It can be seen that A, the concentration is somewhat unsure due to a baseline different from zero (maybe due to Troponin leakage emanating from coronary insufficiency), and a slowly increasing value. The maximum amplitude of A is a measure of how large the damage is. However the slope, S, has a zero baseline and a much faster signal response, which makes it suitable for detecting AMI. The maximum slope is also a measure of the size of the damage.

Figure 3A:
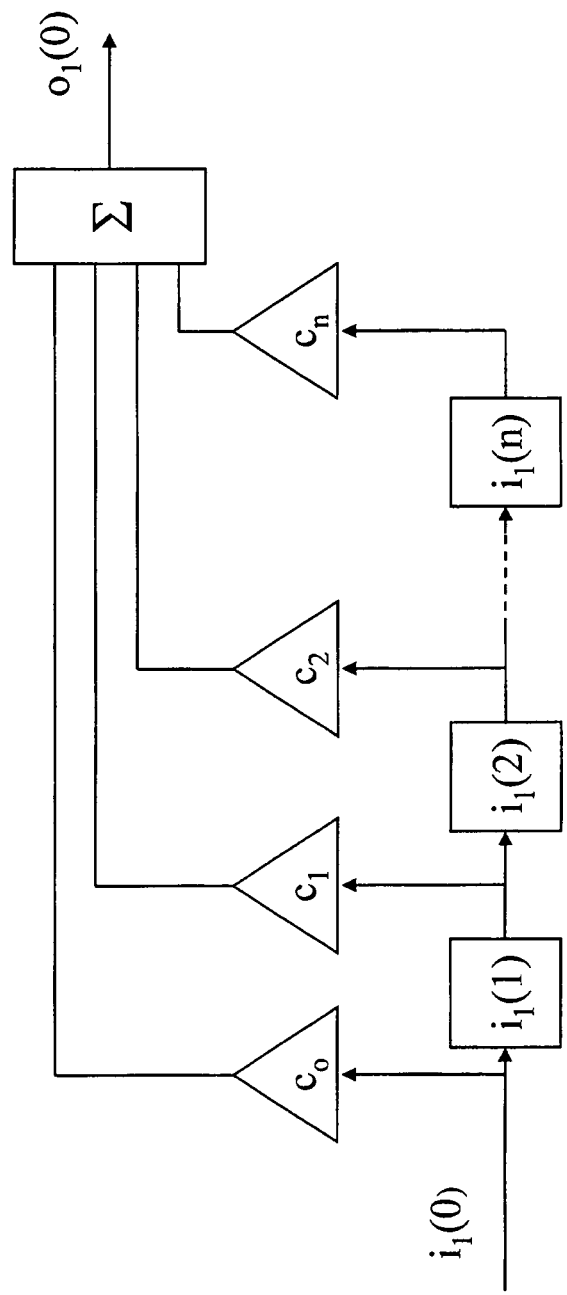
FIG. 3a-c. example of filtering of response signals, a) a FIR-filter, and b) an IIR-filter, c) use of median filters.

FIG. 3a shows a digital filter of the type finite impulse response type (FIR-filter). A FIR-filter is only dependent on an sequence of input signals, here denoted $i_1(t)$, where i stands for input, subscript 1 to p (only 1 shown) for response source 1 to p and the parameter inside the parenthesis is a time index. Boxes with different time index represent time delays, i.e. different samples are used. Triangles represent scaling factors with the actual coefficient inside the triangle. The box with Σ sign denotes summation. The output is denoted o in the same fashion as the input signal.

Figure 3B:
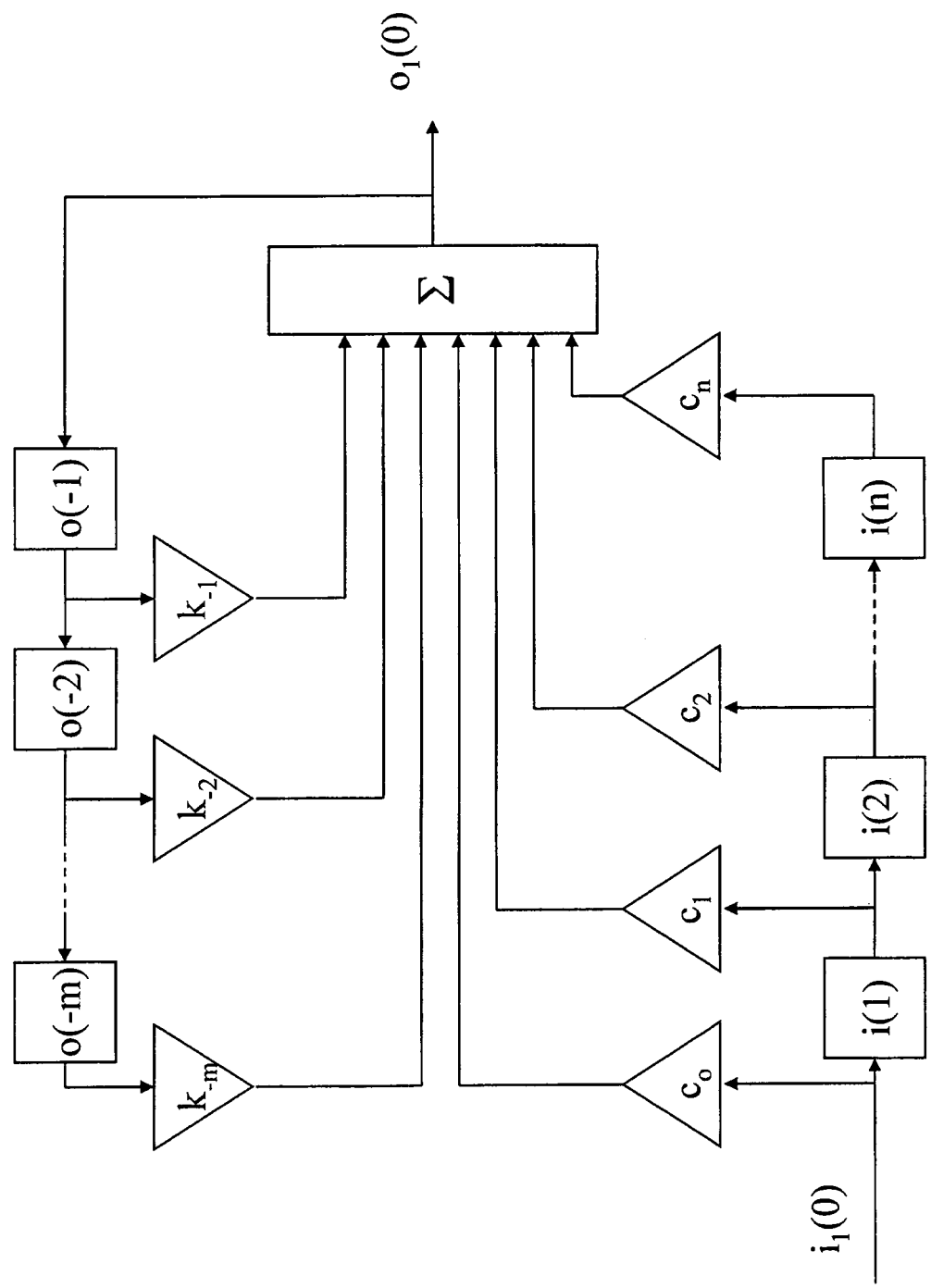

FIG. 3b illustrates an infinite impulse response filter (IIR-filter), which uses output signals in a feedback fashion.

Figure 3C:
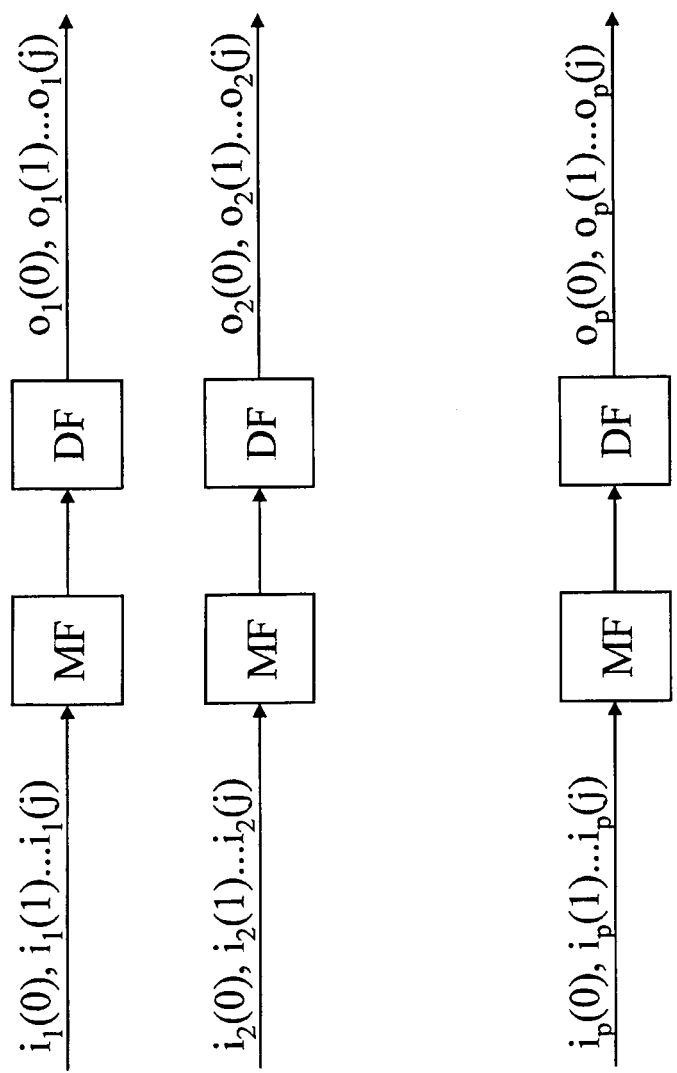

FIG. 3c illustrates how different filters can be combined. First is a median filter. A median filter ranks an ensemble of values and chooses the middle value (in case of even values, the median is the average of the two middle values). This operation effectively eliminates outlayers (values that for some reason are laying far from the correct value. due to noise or errors) completely (as long as there are not a majority of outlayers in the ensemble). An outlayer will influence the output signal, even if the signal is filtered by common digital filter such as moving average, FIR-filters and IIR filters (moving average is a special case of a FIR-filter). It is therefore a large benefit to use a median filter before any other signal processing. The median filer is denoted MF in the figures. The common filters are denoted DF (digital filter). FIG. 3c shows digital filtering of signals from p different response sources, e.g. p different analytes. Both filter parameters and length can be dependent on time, e.g. a heavier filtration can be performed after a certain time or by input signals or mathematical treatment of the input signal such as slope and curvature detection.

Both median filter ant the common filters are preferably implemented in computer software.

Figure 4A:
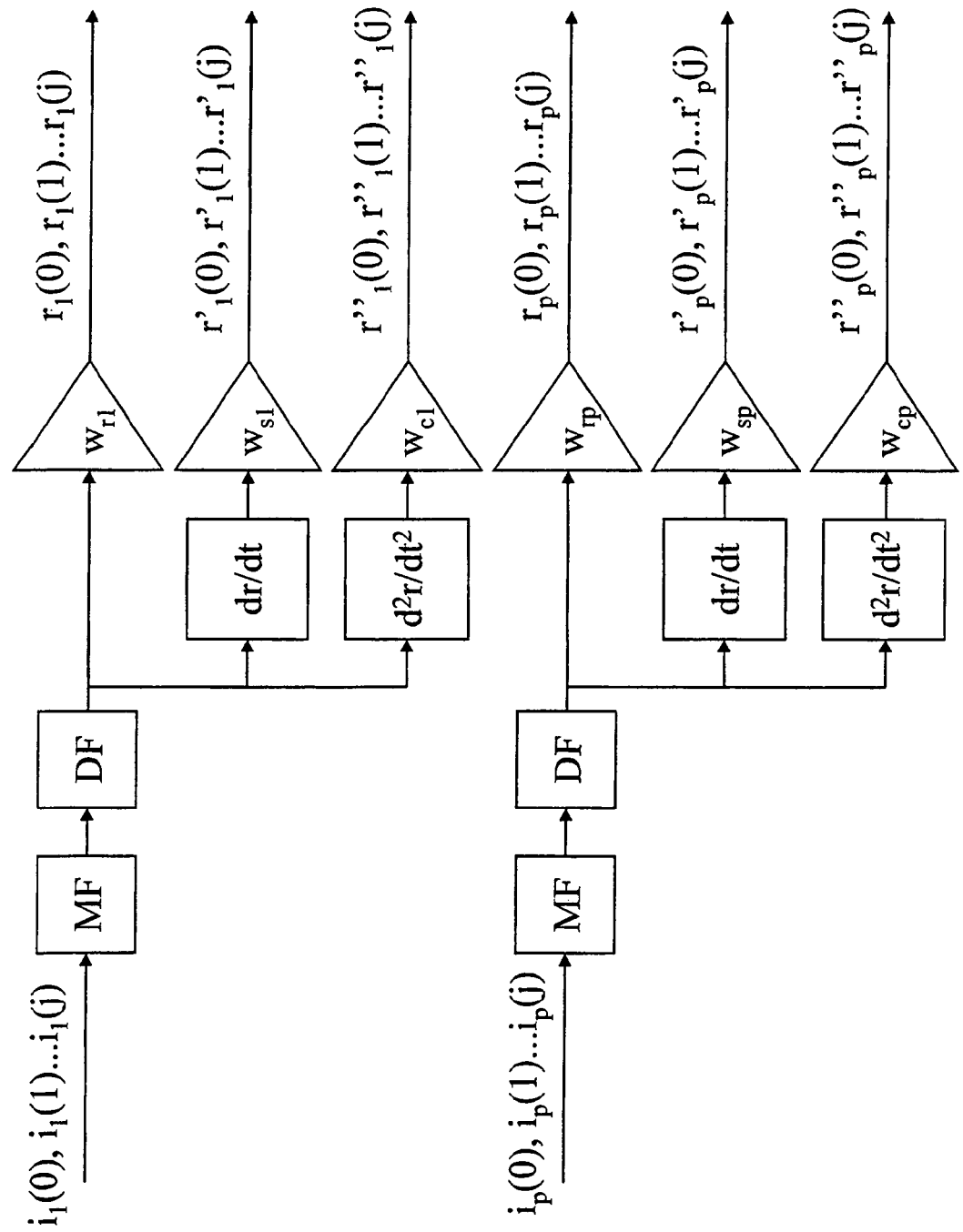
FIG. 4a-d illustrates output signal from response, slope and curvature values from different analytes using weighted sum.

FIG. 4a illustrates a case where the signals from different response sources, denoted i are processed by boxes with dr/dt and $d^2t/dt^2$ to create the slope and curvature values, respectively, from the response sources, The response, slope and curvature is scaled by the coefficients in the triangles, for normalization and easier readability. This is a preferred embodiment for the case of showing parameters that is independent of application and not using the knowledge of prior analyzed cases.

Figure 4B:
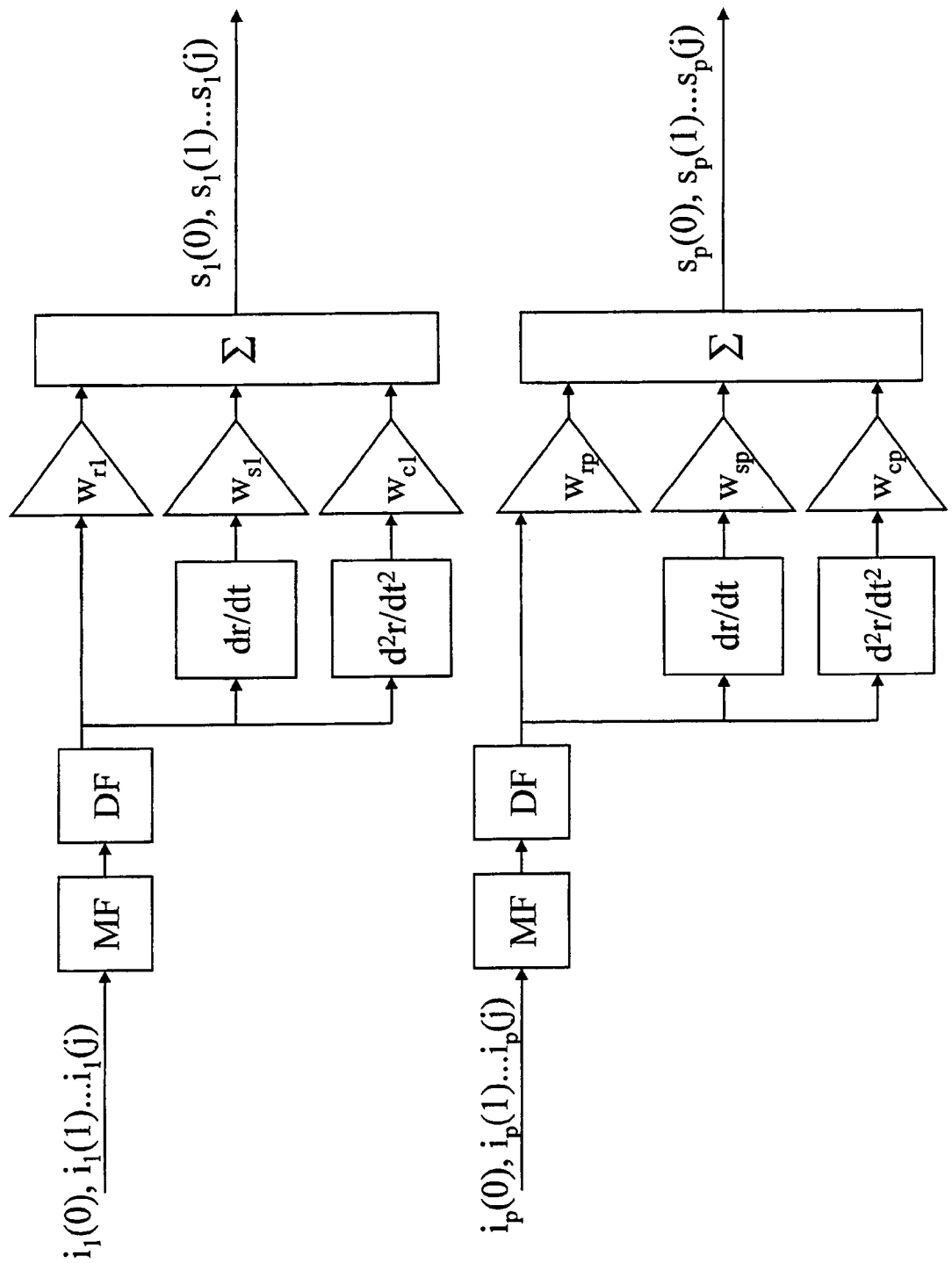

FIG. 4b shows the same configuration as FIG. 4a, but the signals response, slope and curvature are lumped together as a weighted sum for each response source, e.g. analyte. The weight can be negative for one response source, e.g. to detect the when one analyte is decreasing and one analyte is increasing.

Figure 4C:
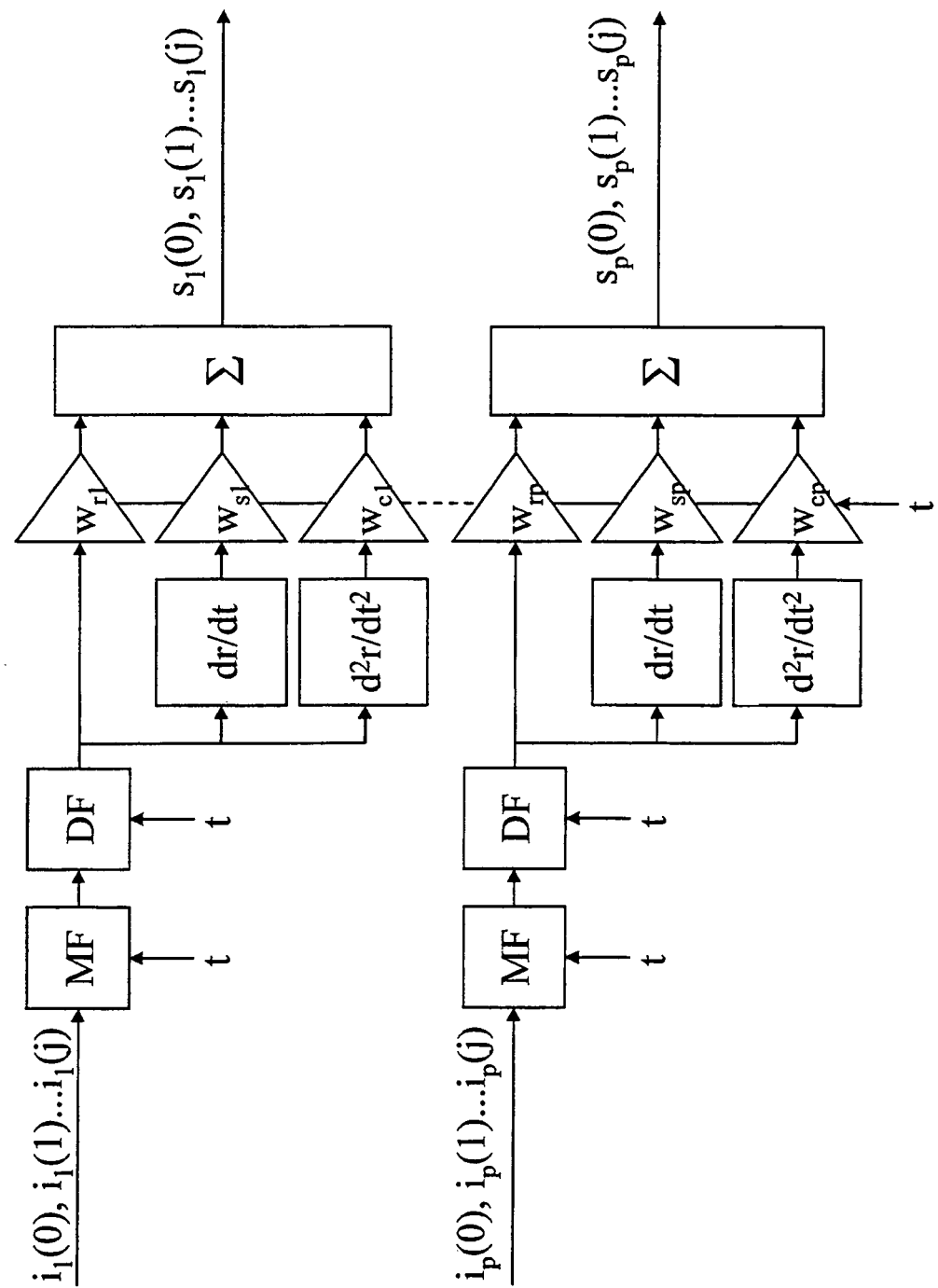

FIG. 4c shows the same configuration as FIG. 4b, but the weights are time dependent. The time dependence can be defined from pain onset or time from thrombolytic therapy for AMI, or some other relevant time point. A scheme can be to initially weight curvature high and then weight the slope high, and at last weight the response high and the others low, highlighting the important clinical relevance of the different signal at different times. An example, in the beginning of an AMI the response is low, but curvature is high and slope is increasing fast. Even though the response is low there is a severe condition. After some time both the curvature and slope is low and the response is high. By using time dependent weights a single signal can be used to quantify the size or severity of the AMI, making decisions easier for physician.

Figure 4D:
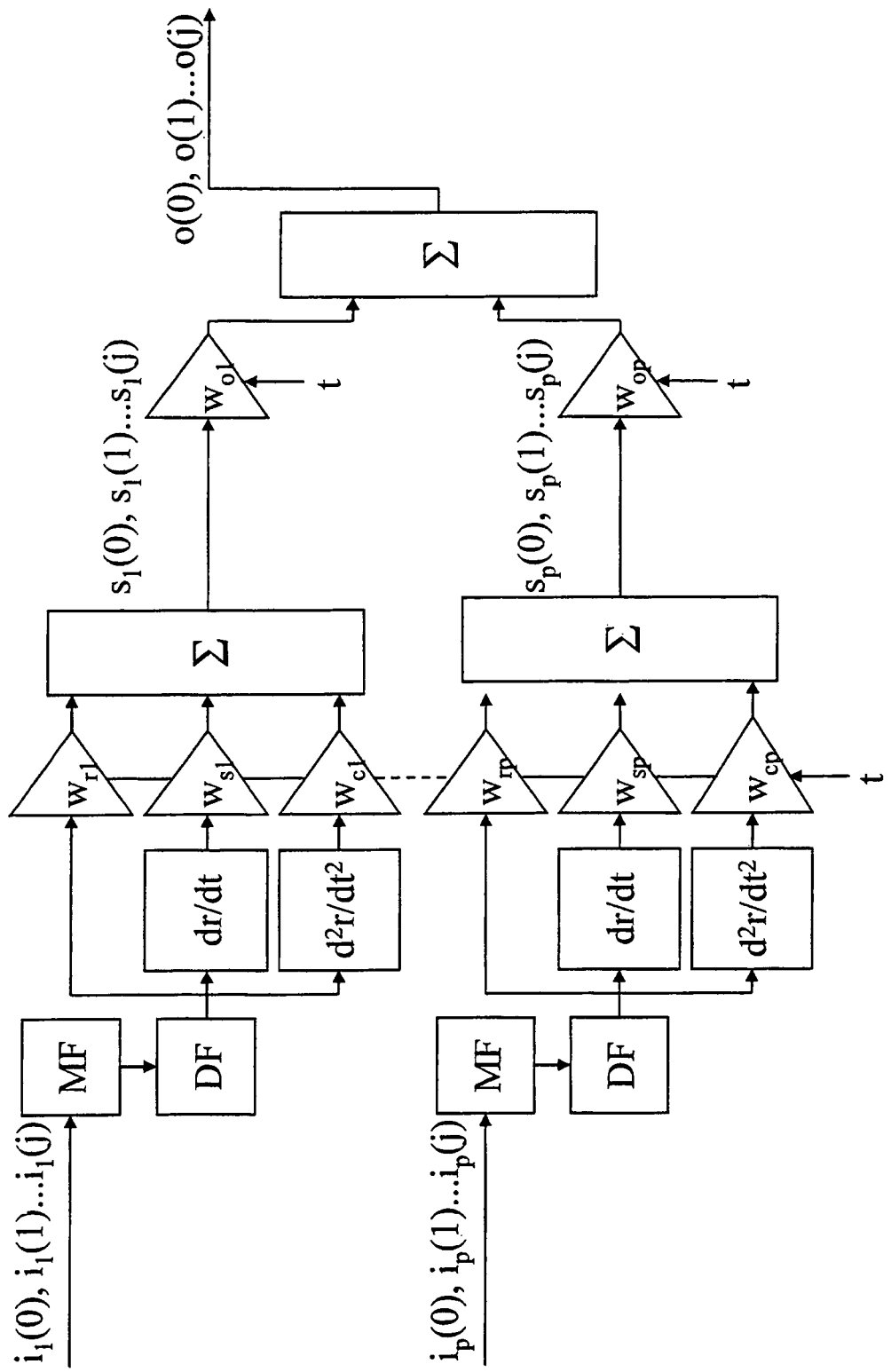

FIG. 4d shows the same configuration as FIG. 4c, but the signals from different response sources, e.g. analytes are lumped together as at least one weighted sum. Coefficients do not necessary have to change over time.

Time dependence of coefficients and parameters can be used for all filtering stages, e.g. a median filter can change the number of time samples it uses, e.g. dependent on time from chest pain, time-base for blood samples, etc.

Example 2

Stroke

During a stroke it is very important to distinguish from ischemic (clot) or hemorrhage (bleeding) stroke. S-100 protein is used as a marker in performing the method according to the invention described herein, and a correct diagnosis is obtained leading to proper treatment of a patient. During thrombolytic therapy of other indications than stroke, it is also important to follow the blood status to avoid hemorrhage stroke.

The invention claimed is:

1. A method of determining health status of a mammal, and depending on the result of said health status determination, making a decision of performing medical treatment, and performing a medical treatment, to change said health status of said mammal, comprising:
   measuring responses from at least one cardiac marker, present in samples of blood repetitively taken from said mammal, wherein a plurality, at least three, of said responses from the same cardiac marker are measured at different times, continuously forming response signals, a curve/curves, with respect to time as long as measurements are taken;
   calculating from said response signals, curve/curves, the rate of change over time and/or the rate of change of said rate of change over time, of said curve/curves, of the responses from said cardiac marker/cardiac markers, continuously presenting new curve/curves, and representing first and/or second derivatives of said response signals, curve/curves;
   wherein said rate of change is based on precise sampling times, less than 1 minute variation of actual sampling time and sampling time used in calculations;
   using the results/results from said calculation for determination of health status of a patient in early stages of a suspected acute medical condition, wherein the suspected acute medical condition is acute myocardial infarction (AMI);
   said decision of performing medical treatment, and performing medical treatment, to change said health status of said mammal is based on the levels of said first derivative signal and/or response signal, and/or said second derivative, where AMI is diagnosed if the level of said response signal, or said first derivative signal or, said second derivative signal, or a combination of these signals, has passed a decision level; and
   performing the medical treatment of opening a closed blood vessel based upon if said first derivative signal or, said second derivative signal, or a combination of these signals, has passed a decision level.

2. The method according to claim 1, wherein said rate of change is based on short time intervals between samples, most preferably, but not limited to, between 10 minutes and 30 minutes, and preferably less than one hour in the initial phase.

3. The method according to claim 1, wherein said responses are filtered by a filter comprising at least one of an average filter, median filter, finite impulse response filter and infinite impulse response filter.

4. The method according to claim 3, wherein said filter comprises a median filter early, preferably first, in the signal processing cascade.

5. The method according to claim 3, wherein filter coefficients and/or parameters and/or filter length change over time.

6. The method according to claim 1, wherein said responses are fitted to one or a plurality of mathematical model/models.

7. The method according to claim 6, wherein said mathematical model consists of two or more exponential functions.

8. The method according to claim 6, wherein said mathematical model includes at least a function of the type Const*$(1-\exp(-t/T1))\exp(-t/T2)$ or type Const*$(1-\exp(-t/T0))(1-\exp(-t/T1))\exp(-t/T2)$, where t is time and T0, T1 and T2 are time constants.

9. The method according to claim 6, wherein a plurality of functions are used and at least one is selected for each of said responses.

10. The method according to claim 9, wherein said function selection is performed with a F-test or with Akaike's Information Criteria (AIC) or with the Corrected Akaike's Information Criteria (AICc).

11. The method according to claim 1, wherein said response is analyte concentration and/or activity.

12. The method according to claim 1, wherein said response is activity.

13. The method according to claim 1, wherein said blood sample is whole blood.

14. The method according to claim 1, wherein said cardiac marker(s) is one or a plurality of recognition molecules that are markers for acute myocardial infarction (AMI), related clinical status due to treatment and exclusion of (AMI), consisting typically of one or a plurality of the following cardiac markers; Troponin-I (TnI), Troponin-T (TnT), Troponin-C (TnC), isoenzyme Creatine Kinase-Muscle Brain (CK-MB), Myoglobin, Lactate Hydro Genase (LHD) isoenzyme, Myosin light chain (MLC), N-terminal pro-B-type natriuretic peptide (NT-proBNP), pro-B-type natriuretic peptide (proBNP), Fatty Acid Binding Protein (FABP), Glycogen Phosphorylase isoenzyme BB (GPBB), high sensitivity C-reactive protein (CRP), urinary Albumin, Interleukin-6 (IL-6), Ischemia Modified Albumin (IMA), Aspartat Transaminase (AST), Hydroxybutyrate dehydrogenase (HBD), drop in iron concentration, enzymatic urinary creatine; markers of test for possible inhibition of treatment: antibody for streptokinase, Plasminogen Activation Inhibitor (PAI-1), Plasminogen Activation Inhibitor (PAI-2); markers of test for clot solving possibility: tissue Plasminogen Activator (tPA), urine Plasmin, Activator (uPA), vitronectin or S-protein, C-protein, antithrombin III.

15. The method according to claim 1, wherein one or a plurality of decision level/levels are based on the levels of one or a plurality of the response/responses and/or the calculated said first derivative/derivatives and/or said second derivative/derivatives from said responses.

16. The method according to claim 15, wherein said decision levels are based on said response and/or of said calculated slope and/or curvature or functions, e.g. first and/or second order derivative/derivatives from said responses.

17. The method according to claim 1, wherein said response, slope and curvature for one or a plurality of cardiac markers, are weighted and summed, creating at least one output signal.

18. The method according to claim 17, wherein said weights for said sum/sums are changing over time.

19. The method according to claim 18, wherein said change of weight over time is related to pain onset of a patient, or time of therapy.

* * * * *